(12) United States Patent
Kantor

(10) Patent No.: US 6,849,062 B2
(45) Date of Patent: Feb. 1, 2005

(54) CATHETER HAVING A LOW-FRICTION GUIDEWIRE LUMEN AND METHOD OF MANUFACTURE

(75) Inventor: John D. Kantor, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 36 days.

(21) Appl. No.: 10/226,340

(22) Filed: Aug. 23, 2002

(65) Prior Publication Data

US 2004/0039332 A1 Feb. 26, 2004

(51) Int. Cl.[7] .................. A61M 31/00; A61M 37/00
(52) U.S. Cl. .................. 604/103.04; 604/528
(58) Field of Search .................. 604/96.01, 103.09, 604/164.13, 264, 265, 523, 524, 528, 915; 606/192–194

(56) References Cited

U.S. PATENT DOCUMENTS

| | | | |
|---|---|---|---|
| 4,406,656 A | 9/1983 | Hattler et al. | |
| 4,601,713 A | * 7/1986 | Fuqua | .......... 604/514 |
| 4,668,221 A | * 5/1987 | Luther | .......... 604/164.03 |
| 4,700,693 A | 10/1987 | Lia et al. | |
| 5,032,113 A | 7/1991 | Burns | |
| 5,163,906 A | 11/1992 | Ahmadi | |
| 5,325,845 A | * 7/1994 | Adair | .......... 600/114 |
| 5,607,404 A | 3/1997 | Khairkhahan | |
| 5,800,414 A | 9/1998 | Cazal | |
| 5,891,111 A | 4/1999 | Ismael | |
| 5,919,163 A | * 7/1999 | Glickman | .......... 604/101.05 |
| 5,935,122 A | * 8/1999 | Fourkas et al. | .......... 604/523 |
| 6,228,110 B1 | * 5/2001 | Munsinger | .......... 623/1.12 |
| 2002/0058963 A1 | * 5/2002 | Vale et al. | .......... 606/200 |
| 2002/0151924 A1 | * 10/2002 | Shiber | .......... 606/194 |

* cited by examiner

*Primary Examiner*—Nicholas D. Lucchesi
*Assistant Examiner*—Catherine S. Williams

(57) ABSTRACT

A catheter shaft for a balloon catheter includes a centrally-located guidewire lumen. A body portion of the catheter shaft includes arc-shaped nodes that define a guidewire track within the guidewire lumen. Each node provides a single contact point for a guidewire within the guidewire lumen, thereby limiting frictional contact due to "rolling" friction, rather than "sliding" friction, between the catheter shaft and an inserted guidewire. The nodes include a crown region that includes the contact point. The crown region may be formed of a material having a lower coefficient of friction than the remaining portion of the catheter shaft. At least one node has an inflation lumen extending therethrough. The inflation lumen is in fluid communication with an interior of an inflatable balloon.

22 Claims, 4 Drawing Sheets

CATHETER HAVING A LOW-FRICTION GUIDEWIRE LUMEN AND METHOD OF MANUFACTURE

BACKGROUND OF THE INVENTION

1. Field of the Invention

This invention relates generally to a medical device. More specifically, the invention relates to a catheter for insertion through a patient's vasculature, the catheter having a low friction guidewire lumen.

2. Background of the Invention

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

One or multiple dilations may be necessary to effectively dilate the artery. In many instances, multiple dilations using multiple "over-the-wire" balloon catheters having balloons with increasingly larger diameters may be required. An over-the-wire catheter is one where a guidewire lumen is provided so that the catheter can be guided to the stenosis site by running the catheter along the guidewire.

Conventional angioplasty guidewire typically include a proximal shaft, an intermediate section and a flexible distal tip. The proximal shaft comprises a solid wire or a solid wall tube. The shaft primarily functions to guide and support a catheter, and to smoothly transmit rotation from the proximal end to an intermediate section.

The intermediate section extends axially from the proximal shaft and generally comprises a tapered core wire surrounded by a coiled spring and typically has more flexibility than the proximal shaft. Like the proximal shaft, the intermediate section must assist in guiding the catheter and smoothly transmitting rotation. However, some degree of flexibility in the intermediate section is desirable to conform the catheter to the curvature of the aortic arch and the coronary arteries.

Extending from the intermediate section at a distal joint is the flexible distal tip that accepts a pre-formed curved shape resembling a "J". The curved tip tends to steer the guidewire in the direction of the hook.

In a typical procedure, a physician will first insert and advance a guidewire to the stenosis site. An initial over-the-wire balloon dilation catheter having a fairly small diameter balloon is then passed over the guidewire to the site and the balloon is inflated to partially dilate the vessel. The balloon is then deflated and the catheter withdrawn. Balloon catheters having progressively larger balloons are then advanced to the stenosis along the guidewire, inflated, deflated, and then withdrawn in succession to sufficiently enlarge the lumen of the artery.

Regardless of whether the balloon catheter is an over-the-wire balloon catheter, all balloon catheters must have an inflation lumen through which a fluid can be forced to pressurize the balloon. As such, in the case of over-the-wire catheters, the catheter must have at least two lumens (viz., a guidewire lumen and an inflation lumen). Catheters having more than one lumen are commonly referred to as "dual-lumen" or "multi-lumen" catheters.

Multi-lumen catheters have cross-sections in a variety of shapes. FIGS. 1 and 2 are examples of prior art, dual-lumen catheter cross-sections. FIG. 1 is a cross-section of a coaxial catheter 100. Coaxial catheter 100 includes an inner tube 102 and an outer tube 104. Inner tube 102 defines an inner lumen or guidewire lumen 108 adapted to receive a guidewire 106. An annular inflation lumen 110 is defined between inner tube 102 and outer tube 104, and is in fluid communication with an interior of a dilatation balloon (not shown).

In use, a guidewire is introduced into a coronary artery and is steered by manipulation of its proximal end, while being observed under a fluoroscope, until the guidewire passes through a stenosis site in the artery. Once the guidewire is in place at the treatment site, a balloon dilatation catheter is advanced over the guidewire, being thus guided directly to the stenosis site so as to place the balloon within the stenosis. Once so placed, the balloon is inflated under substantial pressure to dilate the stenosis.

The anatomy of coronary arteries varies widely from patient to patient. Often a patient's coronary arteries are irregularly shaped and highly tortuous. The tortuous configuration of the arteries may present difficulties to the physician in proper placement of the guidewire, and advancement of the catheter to the site of the stenosis. A highly tortuous coronary anatomy typically will present considerable resistance to advancement of the catheter over the guidewire.

With some types of catheter construction, the increased resistance may cause a tendency for portions of the catheter to collapse or buckle axially. For example, in a catheter having a shaft formed from inner and outer coaxial tubes, such as is shown in FIG. 1, and a balloon mounted to the distal ends of the tubes, there may be a tendency for the tubes to "telescope" when presented with an increase in resistance. The telescoping of the tubes tends to draw the ends of the balloon together slightly, but sufficiently to permit the balloon to become bunched-up as it is forced through the stenosis. This bunching-up of the balloon makes it more difficult for the balloon to access the stenosis site.

Additionally, it is sometimes necessary for the physician to place a torque load on the guidewire in an effort to overcome resistance encountered in a vessel. A torque load applied to a coaxial catheter can cause the outer tube to twist, while the inner tube remains stationary, causing a rotation of the tubes relative to one another.

FIG. 2 shows a cross-sectional view of a non-coaxial, dual-lumen catheter 200. An inflation lumen 202 is in fluid communication with an interior of a dilatation balloon (not shown). A guidewire lumen 204 is defined at least in part by inner tubular member 206 which extends the entire length of the catheter body. A guidewire 208 is shown within guidewire lumen 204. As explained above, a catheter is slid over the guidewire through a tortuous blood vessel. Because guidewire lumen 204 is not coaxial with inflation lumen 202, the guidewire is not centrally located in catheter 200. Thus, when a torque is applied to the catheter to traverse the twists and turns of a body lumen, the catheter does not rotate smoothly. Instead the catheter has a tendency to "flip" in response to an applied torque because the center of gravity of the catheter is not centrally located within the catheter shaft.

When inserting a catheter over a guidewire, friction between the two pieces occurs whenever the guidewire contacts the wall of the catheter's guidewire lumen. If both the guidewire and the guidewire lumen of the catheter have circular cross-sections with substantially equal diameters, as shown in FIGS. 1 and 2, tracking of the catheter over the guidewire is diminished due to friction between the guidewire and the catheter guidewire lumen. Further, in navigating tortuous areas of a vessel where the catheter body is often "flexed," such a guidewire lumen will deform and thereby contact a substantial portion of the outer surface of the guidewire.

Thus, what is needed is a catheter design that overcomes the disadvantages set forth above. Specifically, what is needed is a multi-lumen catheter including both an inflation lumen and a guidewire lumen that is responsive to applied torque loads, without "flipping" or "bunching-up," and that easily tracks over a guidewire due to minimal friction between the guidewire and guidewire lumen.

BRIEF SUMMARY OF THE INVENTION

To achieve the foregoing and other objects, and in accordance with the purposes of the present invention as embodied and broadly described herein, the balloon catheter of the present invention provides a low-friction guidewire lumen which imparts greater strength and better trackability to the catheter. The balloon catheter of the present invention has an elongate shaft with at least one inflation lumen and a non-circular, centrally-located guidewire lumen.

In one embodiment, the guidewire lumen is formed in an essentially "star-shape" with guidewire lumen arms extending toward an outer surface of the catheter shaft. Nodes, arc-shaped portions of the catheter shaft wall that extend into and narrow the guidewire lumen, are situated on either side of the guidewire lumen arms. The nodes each have an innermost point that intersects with and forms a portion of a centrally-located guidewire track. Each guidewire lumen arm extends away from the guidewire track, between each node, to a location of minimum thickness between an outer surface of the catheter shaft and the guidewire lumen.

Each node includes a region comprising a crown, that is an innermost portion of the node, which tangentially intersects with and thereby forms the guidewire track. In one embodiment, the crown is formed of a material different than the material used to form the remaining body portion of the catheter. Accordingly, the catheter is formed of at least two materials. The material used to form the body portion of the catheter provides the requisite burst and tensile strength needed to withstand the inflation pressures and torque that the catheter is subjected to during an angioplasty procedure. Whereas the material forming the crown, in addition to have sufficient burst and tensile strength, is a material having a lower coefficient of friction than the material forming the rest of the body of the catheter. This enables smooth and easy travel over a guidewire within the guidewire lumen. Because of the arc-shape, the crown of each node contacts the guidewire at only a single point in cross-section thereby effectively creating "rolling friction" rather than "sliding friction" between the guidewire and the catheter shaft.

A balloon catheter in accordance with the present invention includes at least one guidewire lumen node having an inflation lumen formed therein which extends from a proximal end of the catheter to an inflatable balloon at the distal end thereof. The inflation lumen is in fluid communication with the balloon. The inflation lumen extends substantially parallel to the guidewire lumen, over a substantial length of the catheter.

In another embodiment of the balloon catheter of the present invention, the catheter shaft includes nodes that each have an inflation lumen formed therein, which is in fluid communication with a dilatation balloon attached thereto. An outer wall of each inflation lumen creates a convex portion on an exterior surface of the catheter shaft. Each convex portion is separated by an arc-shaped indentation, thereby reducing the total surface area of the catheter shaft in contact with a body lumen when such catheter is tracked therethrough. The guidewire lumen of this embodiment is similar to that described above except that the guidewire lumen arms are shallower, thereby increasing the catheter wall thickness.

BRIEF DESCRIPTION OF THE DRAWINGS/ FIGURES

The foregoing and other features and advantages of the invention will be apparent from the following, more particular description of preferred embodiments of the invention, as illustrated in the accompanying drawings.

DETAILED DESCRIPTION OF THE INVENTION

The preferred embodiments of the present invention are now described with reference to the figures where like reference numbers indicate identical or functionally similar elements. While specific materials and method steps are discussed, it should be understood that this is done for illustrative purposes only. A person skilled in the relevant art will recognize that other materials or method steps can be used.

Figure 2:
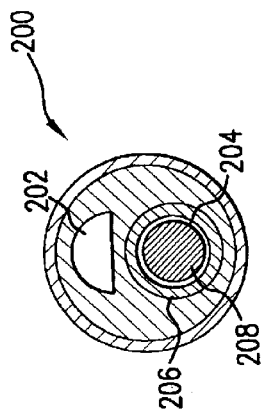
FIG. 2 is a cross-sectional view of a prior art, dual-lumen non-coaxial catheter.
Figure 1:
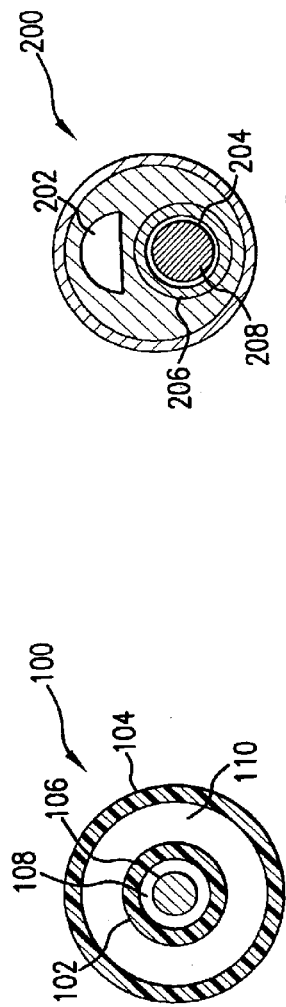
FIG. 1 is a cross-sectional view of a prior art coaxial catheter.
Figure 3:
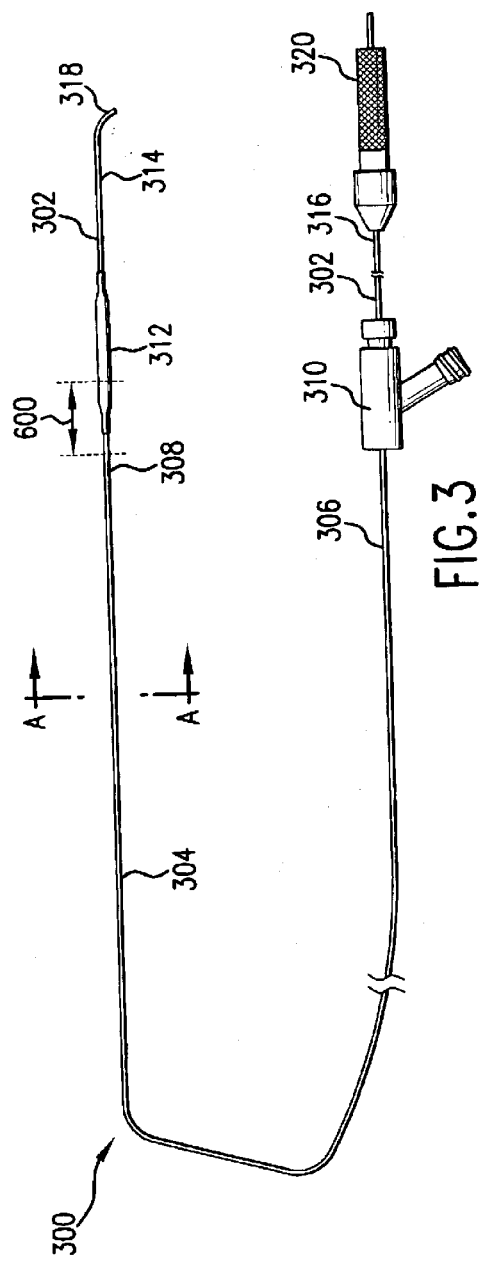
FIG. 3 is a view of a balloon catheter and guidewire assembly according to the present invention.

Referring first to FIG. 3, an embodiment of a dilatation catheter 300 and a guidewire 302 are shown. Dilatation or balloon catheter 300 includes a catheter shaft 304 having a proximal end 306 and a distal end 308. Proximal end 306 of catheter shaft 304 is secured to a luer hub 310. Distal end 308 of catheter shaft 304 is attached to a dilatation balloon 312. An interior of balloon 312 is in fluid communication with an external source of inflation fluid through the length of catheter shaft 304.

Balloon 312 is formed of a thin, pliable material capable of expanding from a compact, collapsed state to an expanded diameter. Balloon 312 may be formed from polyethylene terephthalate (PET) using a drawing and blow molding process, so as to provide biaxial orientation to the material.

PET balloons exhibit the desirable properties of high burst strength and relatively low radial expansion when inflated to high pressures. Alternatively, balloon 312 may be formed from polyethylene, PVC, polypropylene, polyvinyl chloride, nylon, PEBAX or other material, as would be apparent to one skilled in the relevant art. Balloon 312 is approximately 2 cm long and is secured to distal end 308 of catheter shaft 304 by methods known in the art, including gluing, melting or welding.

Guidewire 302 includes a proximal end 316 and a distal end 314. Guidewire 302 passes through a centrally-located guidewire lumen of catheter shaft 304 and extends through balloon 312 of balloon catheter 300. Distal end 314 is more flexible than proximal end 316 for greater maneuverability. The flexibility of distal end 314 may be achieved by tapering guidewire 302 to a reduced diameter at distal end 314, or by constructing distal end 314 from a more flexible material than proximal end 316. Optionally, guidewire 302 may include a spring at distal end 314 that reduces its stiffness relative to proximal end 316. In one embodiment, guidewire 302 is rounded at a tip of distal end 314. In one embodiment, guidewire 302 is a steerable guidewire, as is known in the art, that can be easily manipulated through a tortuous blood vessel.

Distal end 314 of guidewire 302 is bent to one side at a bend 318, as shown in FIG. 3. Bend 318 aids in manipulation and insertion of guidewire 302 through the blood vessel by simplifying the ability to track the guidewire along the proper course at branching vessels. While advancing guidewire 302 to the treatment site, the guidewire itself may be rotated by manipulating proximal end 316. Rotation is readily accomplished by way of guidewire manipulator 320. In one embodiment, guidewire manipulator 320 is a knurled handle which fits over proximal end 316 of guidewire 302 and can be rotated between a physician's thumb and index finger to apply torsion loads, and pushed and pulled to apply axial loads.

In use, guidewire 302 is introduced into a blood vessel through an incision and tracked through the blood vessel, uses radiopaque markers as well as known in the art, to a location just past the target site. Balloon catheter 300, which includes the centrally-located guidewire lumen, is back-loaded onto guidewire 302 and guided through the blood vessel over guidewire 302 until properly positioned, with balloon 312 located within the region of stenosis. Guidewire 302 may then be removed by withdrawing it out of the proximal end of balloon catheter 300 through luer hub 310. Balloon catheter 300 is thereby positioned within the blood vessel for use to treat the stenosis. Optionally, the angioplasty procedure may be performed without removing the guidewire from the guidewire lumen of the balloon catheter.

Figure 4:
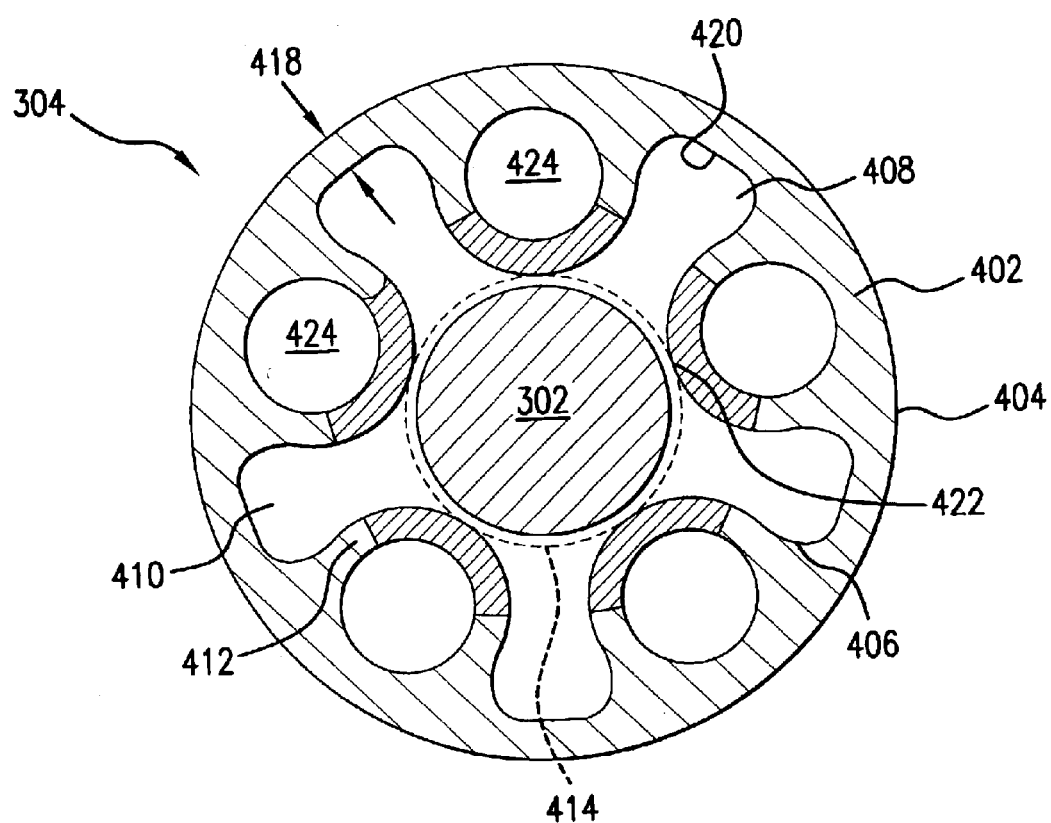
FIG. 4 is a cross-sectional view of an embodiment of the present invention taken along line A—A of FIG. 3.

FIG. 4 shows a cross-sectional view of an embodiment of catheter shaft 304 taken along line A—A in FIG. 3. As shown in FIG. 4, catheter shaft 304 includes a body portion 402. Body portion 402 is formed from a solid, yet flexible material, such as nylon. Nylon is a flexible material which imparts a balloon catheter constructed therefrom with a high impact strength and a high burst strength. Such a catheter constructed from nylon is also fit for use in a wide range of temperatures, exhibits good chemical resistance and good bio-compatibility. However, body portion 402 may be constructed from any other material suitable for a catheter body, such as polymeric materials including: silicone rubber, polypropylene, polyethylene, polyvinylchloride, fluoropolymers and the like, as would be apparent to one skilled in the relevant art.

Body portion 402 is flexible along its length, and has a substantially fixed outer diameter so that the size of the catheter body is substantially consistent along its length. In an alternate embodiment, catheter body portion is tapered along its length, or optionally, only along a distal region thereof, to impart increased flexibility to the distal end. In another embodiment, distal end 308 of catheter body portion 402 is comprised of a more flexible material than proximal end 306 of catheter body portion 402.

Body portion 402 comprises an exterior wall surface 404 and an interior wall surface 406. In the embodiment shown in FIG. 4, exterior wall surface 404 has a substantially circular cross-section with a fixed outer diameter. In one embodiment exterior wall surface 404 of body portion 402 has an outer diameter between 0.030 and 0.080 inch, and in another embodiment between 0.030 and 0.058 inch. However, as stated above, the outer diameter at different locations along balloon catheter 300 may vary if catheter shaft 304 is tapered along its length.

Interior wall surface 406 of catheter shaft 304 forms a non-circular central guidewire lumen 408. In the embodiment shown in FIG. 4, guidewire lumen 408, formed by interior wall surface 406, is substantially star-shaped, having a plurality of guidewire lumen arms 410 extending between nodes 412. Nodes 412 are part of body portion 402 and extend between and define guidewire lumen arms 410. Together, nodes 412 and arms 410 form a guidewire track 414 in guidewire lumen 408. Guidewire track 414 is a theoretical circular perimeter (shown in dashed lines) intersecting an innermost point of each node 412. The diameter of guidewire track 414 is a maximum diameter that a guidewire for use in the balloon catheter of the present invention can be and still fit within the guidewire lumen.

Guidewire lumen arms 410 extend from guidewire track 414 of guidewire lumen 408 toward exterior wall surface 404 to form a location of minimum wall thickness between exterior wall surface 404 and interior wall surface 406, as is shown at reference numeral 418. In one embodiment, minimum wall thickness 418 is within the range of 0.0010 inch to 0.0080 inch, and in another embodiment, minimum wall thickness 418 is within the range of 0.0015 inch to 0.0060 inch. However, minimum wall thickness 418 may vary depending on the desired outer diameter of body portion 402, the length of arms 410, and the desired diameter of guidewire track 414. Minimum wall thickness 418 enables body portion 402 to be flexible; aiding in the insertion of catheter 304 through a patient's tortuous blood vessels.

In one embodiment, guidewire lumen arms 410 include a basal surface 420 that lies generally concentric with exterior wall surface 404. Basal surface 420 provides a relief between adjacent nodes for stress that would be incurred if arms 410 formed points, or, in other words, if adjacent nodes came together to form a point. Although basal surface 420 is shown substantially concentric with exterior wall 404, basal surface need not be concentric with exterior wall 404, but may be non-concentric, may be planar, or may have an arc-shape or any other shape that would form a stress relief, as would be apparent to one skilled in the relevant art. Additionally, arms 410 may have a consistent width, or may taper in either a direction away from guidewire track 414 or in a direction toward guidewire track 414. Finally, arms 410 need not extend "deep" between nodes 412, but may be indentations or curves that separate nodes 412, thereby increasing the minimum wall thickness shown at 418.

Nodes 412 are arc-shaped extensions of body portion 402 that extend into and narrow guidewire lumen 408. Nodes 412 are separated from each other by guidewire lumen arms 410. Nodes 412 are convex-arcs, each of which has an innermost point that forms a portion of guidewire track 414 such that guidewire 302 slides thereon.

In the embodiment of FIG. 4, each node includes an innermost region comprising a crown 422. Crown 422 includes the innermost point of node 412, which intersects with, and thereby forms a portion of, guidewire track 414. Crown 422 extends outward from the point of intersection with guidewire track 414, toward exterior wall surface 404. The distance that crown 422 extends is not a critical factor of the invention of this embodiment, but crown 422 includes the point of intersection of node 412 with guidewire track 414. In this embodiment, crown 422 is formed of a material different than the material of the rest of body portion 402, as is denoted by the cross-hatching in FIG. 4. Accordingly, in this embodiment, catheter 304 is formed of at least two materials.

In the embodiment shown in FIG. 4, the material of crown 422 forms all of crown 422. As such, only node 412 is formed of two materials. However, as would be apparent to one skilled in the relevant art, all of node 412 could be formed of one material and the remaining material of body portion 402 could be formed of a second material.

In one embodiment, crown 422 is formed of a material having a lower coefficient of friction than the material forming the rest of body portion 402. One material meeting this criteria is HDPE, viz., high density polyethylene. However, any other material having a similar or lower coefficient could be used. Other materials, such as TEFLON, polypropylene and polyethylene could be used to form crown 422 as would be apparent to one skilled in the relevant art.

Guidewire 302 is disposed within guidewire lumen 408. In one embodiment, guidewire 302 has a diameter that is slightly smaller than the diameter of guidewire track 414 to minimize the friction and contact between crown 422 of node 412 and guidewire 302. In a preferred embodiment, each crown 422 contacts guidewire 302 at only a single point in cross-section.

During use, crown 422 of each node 412 engages guidewire 302 as the catheter is advanced there over, providing low-friction contact between guidewire 302 and dilatation catheter 300. The material of crown 422, having a low coefficient of friction, allows the catheter of the present invention to be advanced around sharper bends with substantially less axial force than is required to advance standard catheters due to "rolling" rather that "sliding" friction between the catheter of the present invention and the guidewire.

In the embodiment of FIG. 4, each node 412 includes an inflation lumen 424 formed therein. Each inflation lumen 424 extends from proximal end 306 of catheter shaft 304 to inflatable balloon 312 attached to distal end 308 of catheter shaft 304.

Inflation lumens 424 are in fluid communication with the inflatable balloon of the balloon catheter, and are used to inflate and deflate the balloon. After the balloon catheter is properly positioned in a blood vessel, an inflation fluid is forced through at least one inflation lumen 424 to inflate the balloon, forcing the balloon to expand against the interior of the blood vessel. After expansion, the balloon is deflated either through the same inflation lumen used for inflation.

Inflation lumens 424 are isolated from each other and from guidewire lumen 408, such that they do not fluidly communicate with each other within catheter shaft 304. Inflation lumens 424 extend substantially parallel to guidewire lumen 408, substantially the length of catheter shaft 304. Furthermore, inflation lumens 424 are constructed to be structurally sound, in that the inflation lumens maintain their original diameter even when under pressure. As such, the outer diameter or the circumference of catheter shaft 304 does not vary when inflation lumens 424 are pressurized.

In other embodiments, the catheter shaft of the present invention includes three, four, five, six or a greater number of nodes and guidewire lumen arms. Additionally, each node need not include an inflation lumen extending there through.

In one embodiment, the dilatation catheter of the present invention includes seven nodes with only one inflation lumen extending through one of the nodes. The remaining six nodes do not include an inflation lumen, and may be solid or configured for another purpose, such as introduction of dye to a distal end of the catheter.

Figure 5:
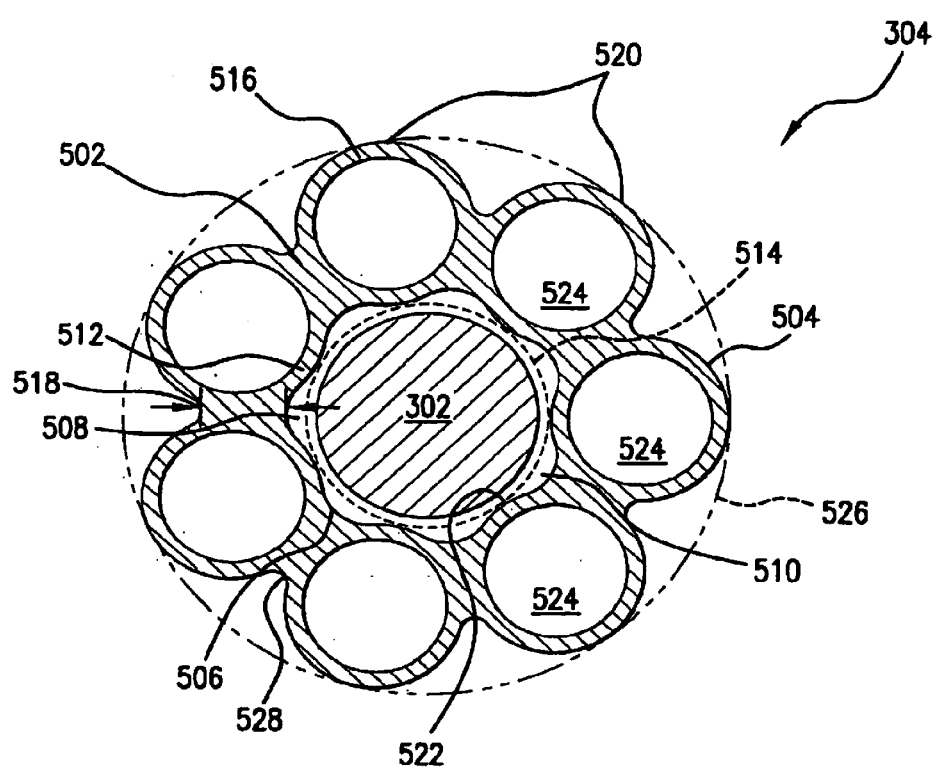
FIG. 5 is a cross-sectional view of another embodiment of the present invention taken along line A—A of FIG. 3.

Another embodiment of catheter shaft 304 of the present invention is shown in FIG. 5. FIG. 5 shows a cross-sectional view of catheter shaft 304 taken along line A—A of FIG. 3. This embodiment of catheter shaft 304 has an exterior wall surface 504 and an interior wall surface 506 forming a centrally located non-circular guidewire lumen 508. Catheter shaft 304 may be formed of the same materials and may include the same physical characteristics and properties as the embodiment described with reference to FIG. 4.

Interior wall surface 506 includes nodes 512 and guidewire lumen arms 510, that form guidewire lumen 508. In this embodiment, catheter shaft 304 includes seven nodes 512 and seven guidewire lumen arms 510, creating a peak-and-valley cross-section. Nodes 512 are arc-shaped, convex walls that extend into and narrow guidewire lumen 508.

Nodes 512 are convex-arcs that each have an innermost point that intersects with and defines a theoretical guidewire track 514 (shown in dashed line). Arms 510 of guidewire lumen 508 extend from guidewire track 514 of guidewire lumen 508 toward exterior wall surface 504 to form a location of minimum thickness 518 between exterior wall surface 504 and guidewire lumen 508.

In one embodiment, arms 510 include a smooth concave surface that lies generally between each convex-shaped node 512. The smooth concave surface eliminates stress risers, which reduces the chance of separation of one node from another and reduces the incidence of crack propagation during manufacturing. However, arms 510 need not be convex-shaped arcs, but could be angled, tapered or otherwise curved, as would be apparent to one skilled in the relevant art.

As described above with reference to FIG. 4, each node includes a region comprising a crown 522. Crown 522 includes the innermost point of node 512, which intersects with guidewire track 514. Crown 522 extends outward from the point of intersection with guidewire track 514, toward exterior wall surface 504. As described above with reference to FIG. 4, crown 522 may be formed of a material different than the material of the rest of catheter shaft 304 (not shown). Accordingly, catheter shaft 304 could be formed of at least two materials.

When formed of two materials, the material in the region of crown 522 may be used to form only crown 522, or the entire node 512. As such, all of node 512 may be formed of one material and the remaining material of catheter shaft body portion 502 could be formed of a second material, or node 512 could be formed of two or more materials.

In one embodiment when catheter shaft 304 is formed of two materials, crown 522 is formed of a material having a lower coefficient of friction than the material forming the rest of catheter shaft 304, such as is described above with reference to the embodiment shown in FIG. 4.

FIG. 5 also shows guidewire 302 in guidewire lumen 508. The guidewire has a diameter slightly less than the diameter of guidewire track 514. In a preferred embodiment, crown 522 of each node 512 contacts guidewire 302 at only a single point in cross-section. Crown 522 of each node 512 engages guidewire 302 as dilatation catheter 300 is advanced over the guidewire, to provide a low-friction contact between the guidewire and the dilatation catheter. The material of crown 522, having a low coefficient of friction, allows the catheter to be advanced over sharper bends with substantially less axial force than is required to advance standard catheters. Furthermore, nodes 512 form bumps that enable the guidewire to roll over the nodes as the catheter is advanced over the guidewire. This results in much less friction than sliding the guidewire in a smooth inner lumen.

In the embodiment of FIG. 5, each node 512 includes an inflation lumen 524. Each inflation lumen 524 extends from proximal end 306 of catheter shaft 304 to inflatable balloon 312 attached to distal end 308 thereof.

At least one of inflation lumens 524 is in fluid communication with inflatable balloon 312 of the balloon catheter of the present invention, and is used to inflate/deflate the balloon. Inflation lumens 524 are isolated from each other and from guidewire lumen 508 within catheter shaft 304. Inflation lumens 524 extend substantially parallel to guidewire lumen 508, substantially the length of catheter shaft 304. Furthermore, the inflation lumens are constructed to be structurally sound, in that the inflation lumens maintain their original diameter even when under pressure. As such, the outer diameter or the circumference of the catheter shaft does not vary when inflation lumens 524 are pressurized.

In this embodiment, exterior wall surface 504 of catheter shaft 304 includes exterior nodes 516. Exterior nodes 516 are convex-shaped arcs that extend from body portion 502. As shown in FIG. 5, exterior nodes 516 are merely the exterior walls of each inflation lumen 524. As such, the convex shape of exterior nodes 516 is concentric with the inflation lumen. However, as would be apparent to one skilled in the relevant art, the shape of exterior nodes 516 need not be concentric with inflation lumens 524.

As stated above, the exterior nodes are the exterior walls of each inflation lumen 524. In one embodiment, the exterior wall of each inflation lumen has a thickness in the range of 0.0010 to 0.0080 inch, in another embodiment the thickness is in the range of 0.0015 to 0.0060 inch. The interior wall between inflation lumen 524 and node 512 may have the same thickness, or may be thicker or thinner depending on the material used to form the catheter shaft, as would be apparent to one skilled in the relevant art.

The outermost point 520 of each exterior node 516 forms a theoretical circular perimeter 526 of dilatation catheter 300, as is denoted by the dashed line in FIG. 5.

Exterior wall surface 504 includes regions between each exterior node 516 that form indentations 528. Indentations 528 are formed by the curves of exterior nodes 516 and extend toward the interior of dilatation catheter 300 within outer diameter 526. In one embodiment, the deepest point of each indentation 528 is an arc formed between, and connecting two exterior nodes 516 disposed on either end of each indentation 528. The arc eliminates stress risers, which reduces the chance of stress fractures and crack propagation that may result in the separation of one node from another. However, in further embodiments it may be advantageous to form the indentations to a point, or to be squared-off, or otherwise shaped, as would be apparent to one skilled in the relevant art.

Indentations 528 allow catheter shaft 304 of balloon catheter 300 to be more flexible and enable easier tracking over a guidewire in a tortuous blood vessel. Additionally, when balloon catheter 300 is introduced into a patient's blood vessel through a guide catheter, indentations 528 provide additional "open area" between the guide catheter and exterior wall surface 504 thereby easing insertion and travel of the catheter therethrough. An increase in the open area also allows increased flow rates of dye injection or other injection through the lumen of the guide catheter for diagnostic purposes.

In other embodiments, dilatation catheter 300 includes between three and eight, or a greater number of nodes and arms. Additionally, as described with reference to FIG. 4, each node need not include an inflation lumen extending therethrough. In one embodiment, the catheter includes seven nodes and only one inflation lumen extending through one of the nodes. The other six nodes include no inflation lumen, but are solid nodes. As stated above with reference to FIG. 4, the catheter of the present invention includes an odd number of nodes that form the guidewire track. Nevertheless, the catheter of the present invention could have an odd or an even number of nodes. Dilatation catheter 300 is compatible with guide catheters smaller than 6 French, but may be used with larger catheters, as would be apparent to one skilled in the relevant art.

Catheter shaft 304 of the present invention is attached to balloon 312 such that the inflation lumens thereof are in fluid communication with the interior of the balloon. Accordingly, the balloon is inflated or deflated through the inflation lumens. Attachment of balloon 312 to catheter shaft 304 is shown and described with reference to FIG. 6.

Figure 6:
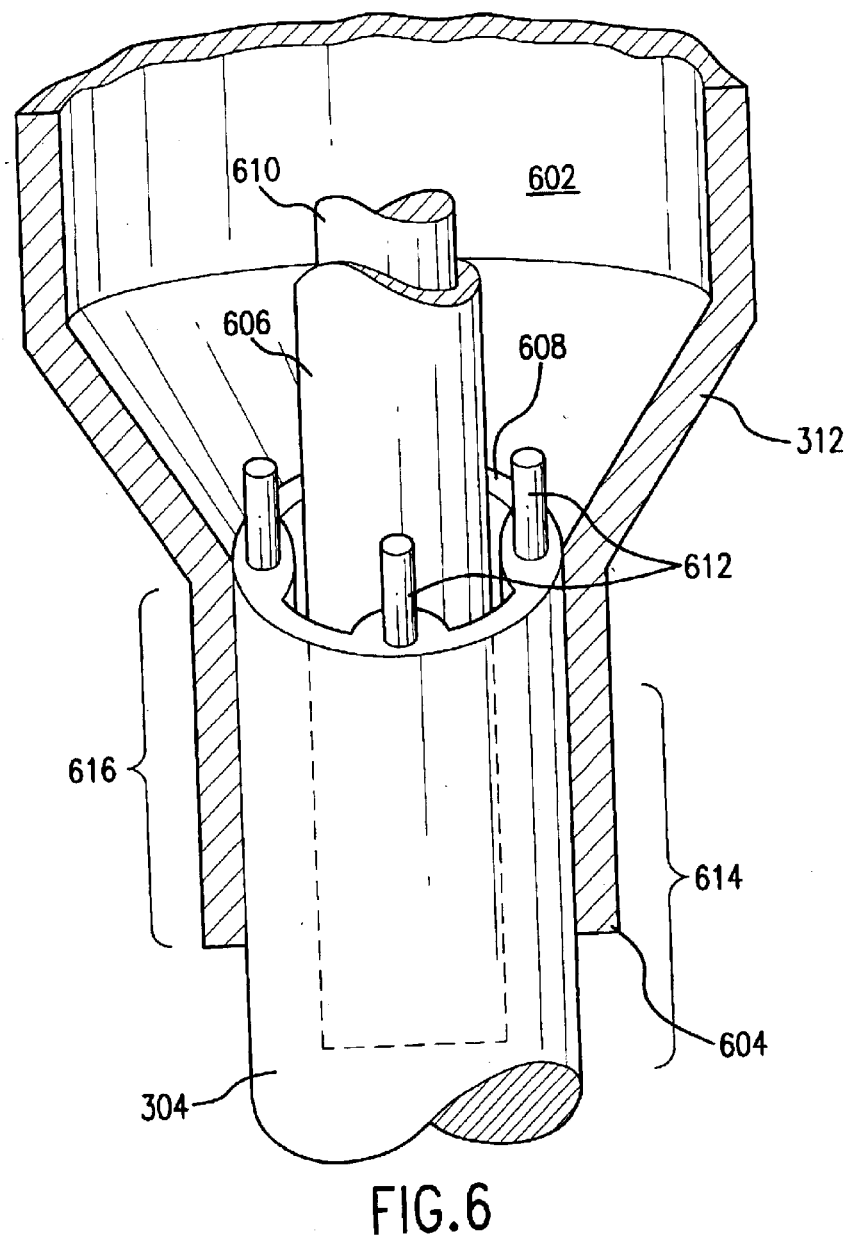
FIG. 6 is a perspective view of a portion 600 of the balloon catheter of FIG. 3, including mandrels used to form the bond between a catheter shaft made according to the present invention and the balloon.

A portion of distal end 308 of catheter shaft 304 and balloon 312, are shown in FIG. 6. In order to better view the attachment of balloon 312 to distal end 308 of catheter shaft 304, balloon 312 is shown in cross-section. Catheter shaft 304 is the catheter shaft shown and described above with reference to FIG. 4, except that catheter shaft 304 has only four nodes. However, as would be apparent to one skilled in the relevant art, the catheter shaft of FIG. 5 could also be assembled using the same method and technique.

Balloon 312 includes a proximal end 604 and distal end (not shown). Balloon 312 forms an interior chamber 602 which is in fluid communication with the inflation lumens of catheter shaft 304. Catheter 300 includes an inner member 606. Inner member 606 extends into distal end 308 of catheter shaft 304, as shown by the dashed lines. Inner member 606 extends from distal end 308 of catheter shaft 304, through balloon 312, and out the distal end of the balloon. As will be explained below, the distal end of the balloon is sealed about a distal end of inner member 606, sealingly closing balloon 312. Inner member 606 forms a guidewire lumen that extends through balloon 312 and out a distal end thereof (not shown).

Inner member 606 is a tube and is formed of either the same or different material as catheter shaft 304. Inner member should be comprised of a material that is easily bonded to catheter shaft 304. A guidewire mandrel 610 is shown disposed in an interior lumen of inner member 606. Additional inflation lumen mandrels 612 are disposed in the inflation lumens of catheter shaft 304.

During manufacturing, guidewire mandrel 610 is inserted into inner member 606. Inner member 606, along with guidewire mandrel 610, are inserted into the guidewire lumen of catheter shaft 304. Also, inflation lumen mandrels are inserted into the inflation lumens of catheter shaft 304.

One end of balloon 312 is disposed about the exterior of catheter shaft 304. A laser welding unit melts an exterior surface of inner member 606 to an interior surface of catheter shaft 304 along a catheter bond zone 614. Also, the laser welding unit melts balloon 312 to an exterior surface of catheter shaft 304 at a balloon bond zone 616.

During the welding process, the inflation lumen mandrels 612 and the guidewire mandrel 610 maintain the lumens so that they do not become occluded by the melting materials. After the welding process is complete, the inflation lumen mandrels 612 are withdrawn, leaving open passages. Accordingly, the inflation lumens are then in open fluid communication with interior chamber 602 of balloon 312.

After inflation mandrels 612 are removed from catheter shaft 304, the distal end of balloon 312 is welded to the distal end of inner member 606, sealing and enclosing balloon chamber 602. During this welding process, guidewire mandrel 610 is still contained within inner member 606. As explained above, this eliminates any occlusion or diametric change of the guidewire lumen. At completion of the welding process at the distal end of balloon 312 and the distal end of inner member 606, guidewire mandrel 610 is withdrawn through the distal end of inner member 606, and an open guidewire lumen extends from catheter shaft 304, through inner member 606 to the distal end of balloon 312.

Other methods may be used to bond balloon 312 and inner member 606 to catheter shaft 304. For instance, an adhesive or a cement could be used, as well as heat or laser means, as would be apparent to one skilled in the art.

The catheter shaft of the present invention can be manufactured using a number of different extruding methods. One method includes use of two extruders of typical design and configuration that feed a single extruder head or die. The extruders may be of known design such as screw extruders using, for instance, screws typically chosen for the polymers employed in the catheter body. Each of the extruders have control valves which may be operated either as proportional valves or as cut-off valves.

Raw material is placed in each extruder. In one embodiment, the materials used are different materials. For instance, the material that will form the outer layer of the catheter shaft could be comprised of a material which has greater flexibility than the material which will comprises the crowns on the inner portions of the catheter shaft. In one embodiment, the material which comprises the crowns on the inner portions has frictional properties which facilitate guidewire passage and control.

The valves regulate the flow of the polymer to the extruder, which melts the polymer to a semi-molten state. The polymers from each extruder enter the extruder head and exit through a die face. Pressurized air is also independently supplied to the extruder head and exit through the die face for each lumen formed in the catheter body. The pressurized air flowing through the die face insures that the extruded tubing has lumens of predetermined diameter.

The first polymer exits the die face through an outer annular region and the second polymer exits the die face through an inner annular region, or through locations corresponding to the crowns, as would be apparent to one skilled in the relevant art. The semi-molten catheter body is then pulled through a water bath typically using a puller.

While the invention has been particularly shown and described with reference to preferred embodiments thereof, it will be understood by those skilled in the art that various changes in form and detail may be made therein without departing from the spirit and scope of the invention.

What is claimed is:

1. A balloon catheter for insertion into a body lumen, comprising:
   a catheter shaft having a proximal end and a distal end and an exterior surface and an interior surface and a body portion between said interior and exterior surfaces, said catheter shaft including,
   a plurality of nodes formed in said body portion of said catheter shaft and extending from said interior surface, each of said nodes having a crown portion that defines a guidewire track, at least one of said nodes having an inflation lumen extending therethrough, substantially parallel to said guidewire track wherein said nodes form a non-circular guidewire lumen therebetween; and
   a balloon disposed at said distal end of said catheter shaft, wherein said inflation lumen is in fluid communication with an interior of said balloon,
   wherein said catheter shaft is comprised of a first material and each of said crown portions is comprised of a second material that is different than said first material.

2. The balloon catheter of claim 1, wherein said second material has a lower coefficient of friction than said first material.

3. The balloon catheter of claim 1, wherein said second material is high density polyethylene.

4. The balloon catheter of claim 1, wherein said first material is nylon.

5. The balloon catheter of claim 1, wherein each of said plurality of nodes includes an inflation lumen extending therethrough.

6. The balloon catheter of claim 1, wherein said catheter shaft includes five nodes.

7. The balloon catheter of claim 1, wherein said catheter shaft includes seven nodes.

8. A balloon catheter for insertion into a body lumen, comprising:
   a catheter shaft having a proximal end and a distal end and an exterior surface and an interior surface and a body portion between said interior and exterior surfaces, said catheter shaft including,
   a plurality of nodes formed in said body portion of said catheter shaft and extending from said interior surface, each of said nodes having a crown portion that defines a guidewire track, at least one of said nodes having an inflation lumen extending therethrough, substantially parallel to said guidewire track wherein said nodes form a non-circular guidewire lumen therebetween; and
   a balloon disposed at said distal end of said catheter shaft, wherein said inflation lumen is in fluid communication with an interior of said balloon,
   wherein said exterior surface of said catheter shaft includes a plurality of indentations, each of which inwardly extends toward said guidewire track between adjacent nodes.

9. The balloon catheter of claim 8, wherein said plurality of indentations provide open area between said exterior surface of said catheter shaft and a guide catheter when the balloon catheter is inserted therein.

10. The balloon catheter of claim 8, wherein each of said plurality of nodes includes an inflation lumen extending therethrough.

11. The balloon catheter of claim 8, wherein said catheter shaft includes five nodes.

12. The balloon catheter of claim 8, wherein said catheter shaft includes seven nodes.

13. A catheter and guidewire assembly, comprising:
a catheter including,
  a catheter shaft having a distal end and a proximal end, an exterior surface and an interior surface and a body portion between said interior and exterior surfaces, and made of a first material, said catheter shaft including,
  a guidewire lumen defined by at least three convex portions formed in said body portion of said catheter shaft each of which has a crown portion that defines a guidewire path, wherein at least each of said crown portions of said convex portions is comprised of a second material, and
  at least one lumen disposed parallel to said guidewire lumen; and
a flexible guidewire disposed within said guidewire lumen, wherein said guidewire contacts said catheter shaft only along a surface of said crown portions.

14. The catheter and guidewire assembly of claim 13, wherein each of said convex portions is comprised of said second material.

15. The catheter and guidewire assembly of claim 14, wherein said second material has a lower coefficient of friction than said first material.

16. The catheter and guidewire assembly of claim 14, wherein said catheter is a balloon catheter further comprising an inflatable balloon attached to said distal end of said catheter shaft such that said balloon is in fluid communication with said at least one inflation lumen.

17. A catheter and guidewire assembly, comprising:
  a catheter having a catheter shaft with a fixed outer diameter, a distal end and a proximal end, an inner wall surface and an exterior surface, said catheter shaft including,
    a body portion between said inner wall surface and said exterior surface,
    a guidewire lumen, wherein said body portion includes at least three nodes which extend said inner wall surface into said guidewire lumen such that said guidewire lumen has a non-circular guidewire lumen surface, and
    a lumen extending through at least one of said nodes, and disposed parallel to said guidewire lumen; and
  a flexible, removable guidewire, said guidewire being sized to slidingly fit within said guidewire lumen, wherein said guidewire contacts each of said nodes when said catheter is tracked thereover.

18. The catheter and guidewire assembly of claim 17, wherein said catheter shaft is comprised of a first material and said nodes are comprised of a second material different from said first material.

19. The catheter and guidewire assembly of claim 18, wherein said second material has a lower coefficient of friction than said first material.

20. The catheter and guidewire assembly of claim 18, wherein said second material is nylon.

21. The catheter and guidewire assembly of claim 18, wherein said first material is high density polyethylene.

22. The catheter and guidewire assembly of claim 18, wherein said catheter shaft includes a soft tip region.

* * * * *